United States Patent [19]

Majewski et al.

[11] Patent Number: 5,960,057
[45] Date of Patent: Sep. 28, 1999

[54] RADIOLOGY UTILIZING A GAS MULTIWIRE DETECTOR WITH RESOLUTION ENHANCEMENT

[75] Inventors: Stanislaw Majewski; Lucasz A. Majewski, both of Grafton, Va.

[73] Assignee: Southeastern Universities Research Assn., Newport News, Va.

[21] Appl. No.: 08/953,210

[22] Filed: Oct. 17, 1997

[51] Int. Cl.[6] .................................................. G01N 23/04
[52] U.S. Cl. ............................................. 378/62; 378/37
[58] Field of Search .................................... 378/62, 63, 37

[56] References Cited

U.S. PATENT DOCUMENTS 5,005,196  4/1991  Lanza et al. .............................. 378/54
5,189,686  2/1993  Hixson ..................................... 378/37

*Primary Examiner*—Craig E. Church

[57] ABSTRACT

This invention relates to a process and apparatus for obtaining filmless, radiological, digital images utilizing a gas multiwire detector. Resolution is enhanced through projection geometry. This invention further relates to imaging systems for X-ray examination of patients or objects, and is particularly suited for mammography.

5 Claims, 4 Drawing Sheets

Minimum Zoom
Spring On Detector 2 cm Above Detector 11 cm Above Detector

Maximum Zoom
24 cm Above Detector

RADIOLOGY UTILIZING A GAS MULTIWIRE DETECTOR WITH RESOLUTION ENHANCEMENT

The United States may have certain rights to this invenion under Management and Operating Contract DE-AC09-84 ER 40150 from the United States Department of Energy.

BACKGROUND

X-rays and other forms of radiation have traditionally been used in diagnostic medicine with photographic film. This has also been utilized in screening female patients for breast cancer in mammography. While photographic film can provide adequate resolution, it has a number of drawbacks. It is expensive. Its costs being tied to the market price of silver. It requires chemical development, which, even with "high speed" development equipment, is time consuming. The chemical development process generates waste chemicals which must be disposed of properly, or generate environmental problems.

While charged coupled device (CCD's) detectors can be effectively employed in filmless X-ray image detection such detectors are costly, limited in size, and usually require a phosphor coated plate, which is illuminated by the transmitted X-rays and which is captured by the CCD.

X-ray images can also be obtained in other filmless electronic processes, but such processes often present different problems. For example, one of the most important requirements in filmless, digital image formation, in an area such as mammography is to obtain spatial resolution of an X-ray detector on the order of from about 30 to about 50 microns. This severe requirement is difficult to meet by the presently available position sensitive electronic detectors which are potential candidates for fast filmless digital mammography. The practical resolutions obtainable are often limited by the physical phenomena involved in the process of X-ray detection, such as parallax effect due to photon range, conversion point definition due to photoelectron range, and diffusion caused by electron ionization.

The present invention overcomes the deficiencies of the prior art.

DISCUSSION OF THE PRIOR ART

There has been a considerable amount of effort expended on the subject of mammography. Much of this has been by way of improvement of the equipment that is used. For example, U.S. Pat. No. 4,930,143 is directed to a method and device for mammographic stereotactic punction of pathological lesions in the female breast. More specifically this patent relates to X-ray mammography in which the female breast is imaged in two directions in order to provide stereoimaging of a lesion. Parallax displacement is effected by lateral movement of the breast. This facilitates a needle biopsy of the lesion. Photographic film is used to detect and record the image. It should be noted that geometric enlargement of a portion of the images is disclosed in this reference by increasing the distance of the object from the film cassette. This permits magnification but on photographic film.

U.S. Pat. No. 5,142,557 is directed to high resolution mammography through the utilization of an X-ray source, a phosphor screen to receive radiation passing through the breast and producing light in response to the radiation, and a cooled slow scan CCD camera. The signals from the CCD camera are digitized and sent to a high resolution monitor.

U.S. Pat. No. 5,252,830. This patent is directed to a dedicated apparatus and method for emission mammography. The patent teaches the use of radioactive tracers. The detectors employed are gamma ray sensitive and are used in conjunction with a photomultiplier array or an array of avalanch photodiodes.

U.S. Pat. No. 5,003,979. This patent relates to a system and method for the non-invasive identification and display of female breast lesions. The teaching is directed to the use of magnetic resonance and utilizes a computer and software program to aid in the diagnosis.

U.S. Pat. No. 5,289,520 relates to a stereotactic mammography imaging system with a prone position examination table and CCD camera. The system utilizes a phosphor screen which produces light when exposed to radiation passing through the female breast. The CCD camera records the image, which is digitalized. The use of image enhancement computer software can provide magnification, contrast enhancement, and high resolution images.

U.S. Pat. No. 4,807,637 This patent is directed to the use of light or laser to detect breast lesions. The light passing through the female breast falls on a light sensitive detector which provides a shadow image.

U.S. Pat. No. 5,365,562 This patent relates to X-ray imaging and to an improved digital imaging device, and is particularly useful for medical imaging, such as breast imaging. The invention utilizes as detectors phosphor screens, which give off light when contacted by X-rays passing through the object being imaged. A CCD camera records the light from the phosphor screen and the digitized signal is transmitted to a computer. Provision is made for different screens from which can be selected a particular screen which is best used for certain conditions.

U.S. Pat. No. 5,216,250 This patent relates to imaging systems for X-ray examination of patients or objects capable of image enhancement through the use of digital circuitry an software. Particularly the patent discloses and claims a new digital imaging camera for X-ray examination. Coverage is also obtained for the claimed CCD camera in conjunction with a phosphor plate, producing visible light in response to arriving x-radiation impinging thereon, and a diagonally positioned pellicle mirror to reflect the visible light to the focusing means.

SUMMARY OF THE INVENTION

In accordance with the present invention many of the difficulties of filmless digital mammography are overcome through the utilization of a suitable radiation source, such as X-ray, a gas chamber multiwired detector placed a distance from the female breast being studied, which is connected to a suitable computer to digitize the detector signals and a high resolution monitor to display the image.

Preferably, the space between the object breast and the detector is contained and any gas present in this contained space has a "low-z" value (in the case of gasses a low atomic number). Intentional gases are the "low-z" gases. Unintentional gases are contaminant atmospheric gases which have not been completely removed. X-rays are the preferred form of radiation and can be generated from a conventional X-ray tube or from radioactive elements which generate X-rays, such as Fe 55. If this space is not evacuated and/or filled with "low-z" gasses, substantial radiation scattering will occur which will adversely affect the image quality. Additionally, in order to suppress any possible scattered photons, a conventional focusing grid is preferably placed in front of the detector.

In operation the present invention directs radiation such as X-ray through a human female breast which has been compressed by conventional means, the radiation which passes through the breast impinges on a multiwire gas chamber detector, the detector generates signals in response to the radiation falling upon its surface. These signals are digitized and drive a high resolution monitor where the images can be viewed. These signals can be enhanced and possibly screened by suitable computer software, if desired.

BRIEF DESCRIPTION OF THE DRAWINGS

The foregoing advantages, constructions, and operation of the present invention will become more readily apparent from the following description and accompanying drawings wherein.

DETAILED DESCRIPTION OF THE INVENTION

Figure 2:
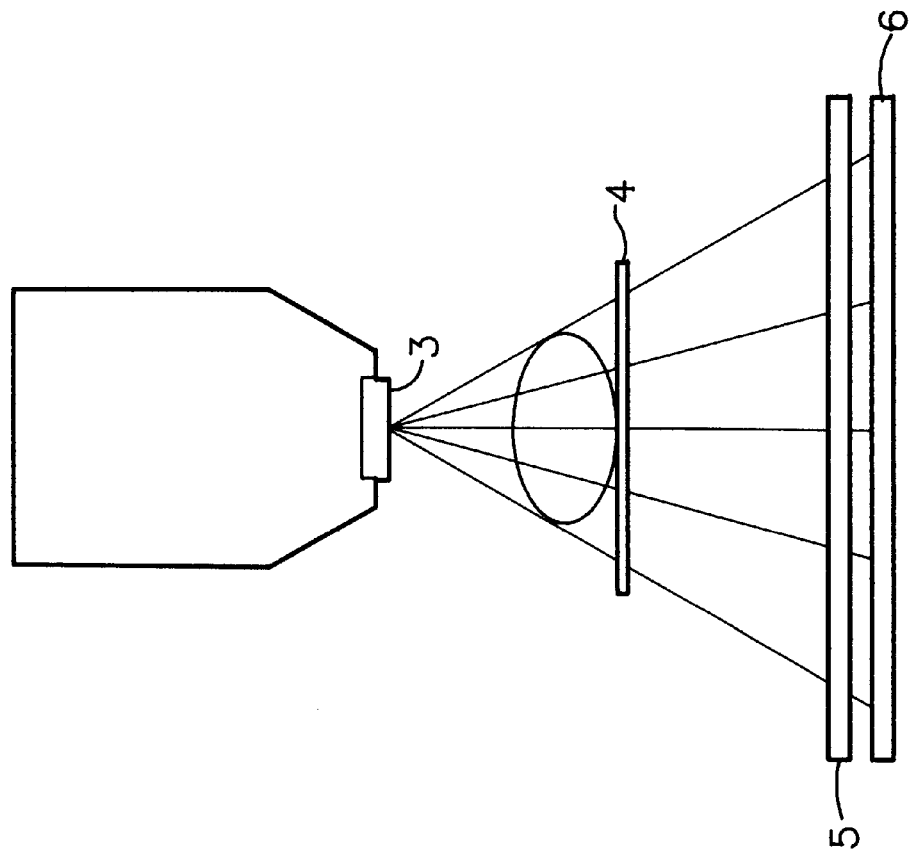
FIG. 2 is a schematic drawing depicting a method and apparatus of the present invention.

Before turning to a detailed consideration of the drawings of this invention it is appropriate at this point to define certain of the terms and parameters of the invention.

The multiwire detector was discovered by Georges Charpak. The principles of the operation of such detectors is discussed in "Lectures given in the Academic Training program of CERN 1975 1976 in Genva" are set forth in a paper by F. Sauli, entitled "Principles of Operation of Multiwire Proportional and Drift Chambers at pages 50 through 53, inclusive, CERN 77-09, dated May 3, 1977. CERN is the European Organization For Nuclear Research. This publication is incorporated herein by reference.

The use of multiwire proportional chambers for X-ray imaging is discussed in a paper by H. J. Besch, R. Gehrke, M. Rost and A. H. Walenta, entitled "A High Rate Multiwire Proportional Chamber with Small Cells for X-ray Imaging at Synchrotron Radiation Sources", published in the Proceedings of the European Workshop on X-ray Detectors for Synchrotron Radiation Sources, Aussole, France, Sep. 30–Oct. 4, 1991. This reference is also incorporated herein by reference.

The multiwire gas chamber detector as used in the present invention is characterized by having the gas chamber containing a gas having properties for gas multiplication and is typically a mixture of argon with additives such as carbon dioxide or hydrocarbons. Examples of such gases are methane, ethanol and isobutane.

A "low-z" gas envelope is used to provide enhanced results with respect to light scattering and absorption of X-rays. It is preferred that the envelope be evacuated, and then filled with the desired "low-z" gas. This, of course, can be repeated a number of times to insure that the presence of unintentional, unwanted "higher" gases is minimized or eliminated.

In the conduct of this invention it is necessary to have a suitable radiation source X-ray radiation is exemplary of such a source and is preferred because it is widely available and considerable experience has been acquired in its use. Gamma radiation can also be employed as a radiation source if adequate care is taken, accelerated particles can also be used, subject to the sensitivity of the detector.

While the invention can be used in mammography, and indeed this is its preferred use, it can be used in industrial applications, such as quality control. This invention can be effectively used in all applications where conventional film x-ray photography is employed.

The focusing grid which is optionally used in the conduct of this invention is a standard device used in X-ray radiography. This grid permits only the selected straight photon beam to proceed through the grid, while all the scattered photons going in directions not aligned with the grid are absorbed by the grid. In this process the signal to background ratio is significantly improved. The standard grid is usually made of lead foil. Other materials can be used in its construction such as tantalum or tungsten.

The grid should be placed relatively close to the detector. The grid function is only to absorb the scattered radiation, and it has no electrical function. Usually, only one grid is used per detector.

In respect to filmless digital mammography one of the most important requirements is to attain a spatial resolution in X-ray detection on the order of 30–50 microns. This severe requirement is difficult to meet by the presently available position sensitive electronic detectors—the candidates for fast filmless digital mammography. The practical resolutions obtainable are often limited by the physical phenomena involved in the process of X-ray detection, such as parallax effect due to photon range, conversion point detection due to photoelectron range, and diffusion of ionization electrons, and the like.

Turning now to a detailed description of the invention with reference to the drawings.

Figure 1:
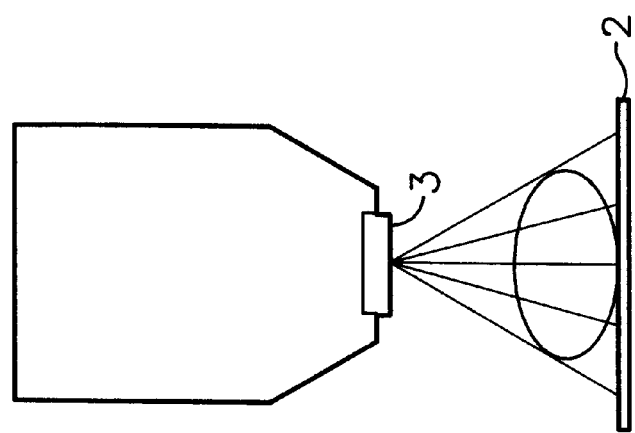
FIG. 1 is a schematic drawing of the conventional method of mammography.

With reference to FIG. 1 the standard source-object-detector geometry used in mammography is to place the studied object 1 as close as possible to the film cassette 2 and use a point x-ray source 3. This geometry can be modified as shown in FIG. 2 where projective geometry is used to magnify the object image at the detector plane. In FIG. 2 an optional support 4 is provided to support the object 1. An optional focusing grid 5 is provided immediately above the multiwire detector 6. If the required detector resolution is Os0 in the standard geometry, the same equivalent resolution will be obtained by placing the detector at a further distance and allowing for an increased detection resolution Os1 by approximately the ratio of the source detector distances (L) in the two cases. The magnification factor is approximately equal to the ratio L1/L0. The increased object-detector distance requires that a larger detector be used, however, for example in the case of gas chambers this is not a major problem (unlike the spatial resolution limit). To limit absorption and scattering of X-rays in the region between the object and the detector, the gas volume in this region is filled with "low-z" gases, such as helium or is simply evacuated of any gas, if practical. If it is required that the thickness of the object traversed by X-rays is minimized to improve detection of small features and minimize scattering, as is the current practice in mammography, an optional light weight support can be used. Another role of the support is to define the projective geometry of the exposure. This support can be made of materials which present little interference to or scattering of X-rays, such as a structure of acrylic foam covered with two thin skins made of carbon fibers. Many other structures having similar characteristics can be used as support.

Figure 3:
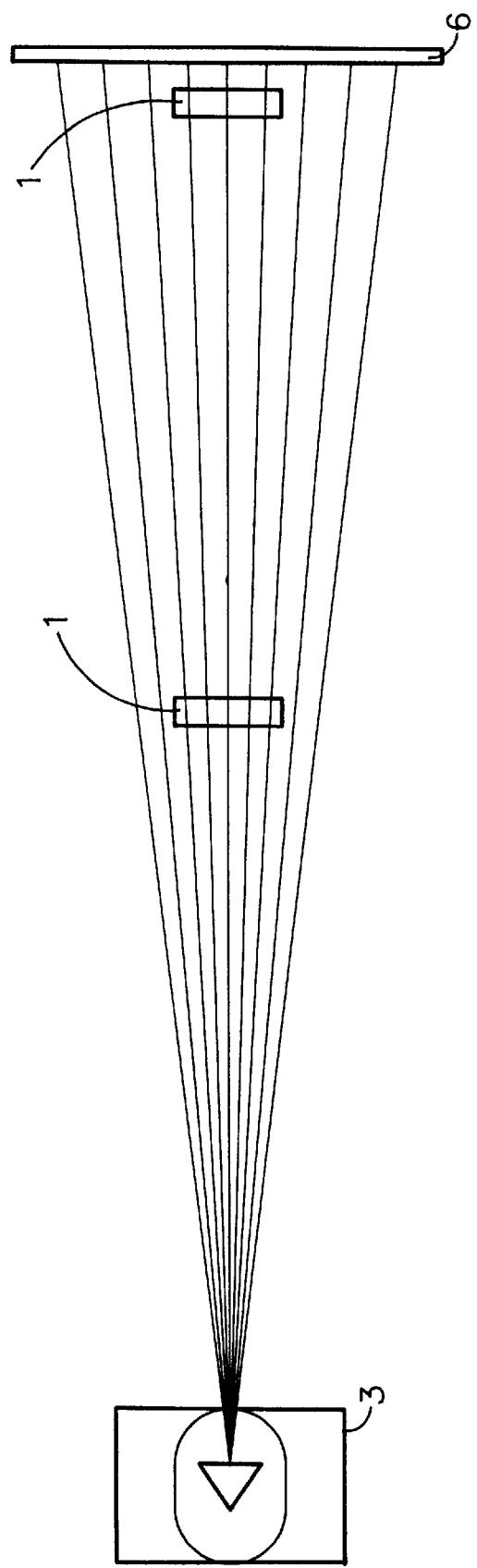
FIG. 3 is a schematic drawing showing the Zoom Magnification Effect of this invention.
Figure 4A:
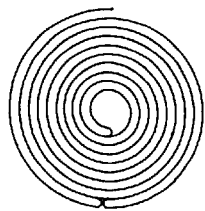
FIG. 4 displays four different images created by moving an object, in this case a metal spring, different heights above the detector to exemplify the Zoom Magnification Effect.
Figure 4B:
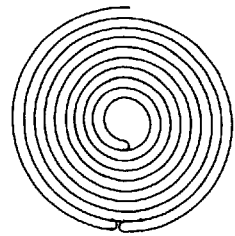
Figure 4C:
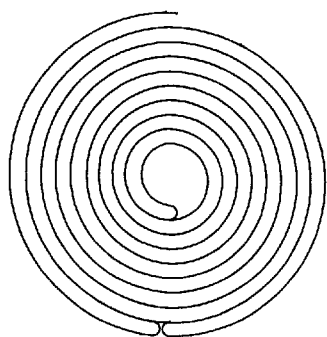
Figure 4D:
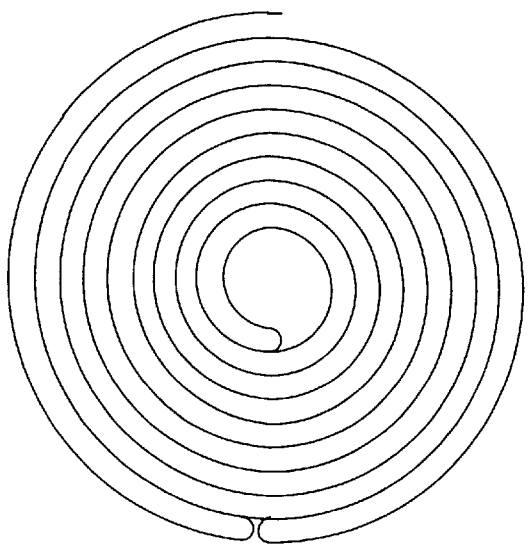

FIG. 3 illustrates the zoom magnification effect wherein the point X-ray source 3, passes through the object 1, in two locations A and B. The object located in position B is essentially unmagnified, while the object located at position A is substantially magnified, when it falls on the detector 6.

FIG. 4, with reference to FIG. 3 above, shows one experimental example of another variant of the projective method (but utilizing the same principle of the resolution enhancement by projective geometry) with the source-detector distance kept constant and the object being moved away from the detector. A multiwire chamber detector (MWPC) of a 0.6 mm r.m.s. resolution was used in this demonstration with 6 keV X-rays from a Fe-55 source. It can be seen how with the increasing "zoom" magnification effect the details which are not visible at the lowest projective factor are becoming evident. Position A and position B are the same as displayed in FIG. 3 above. The object in this example is a metallic spring of 1.0 centimeter diameter. It can be seen that the resolution is increased.

Figure 5:
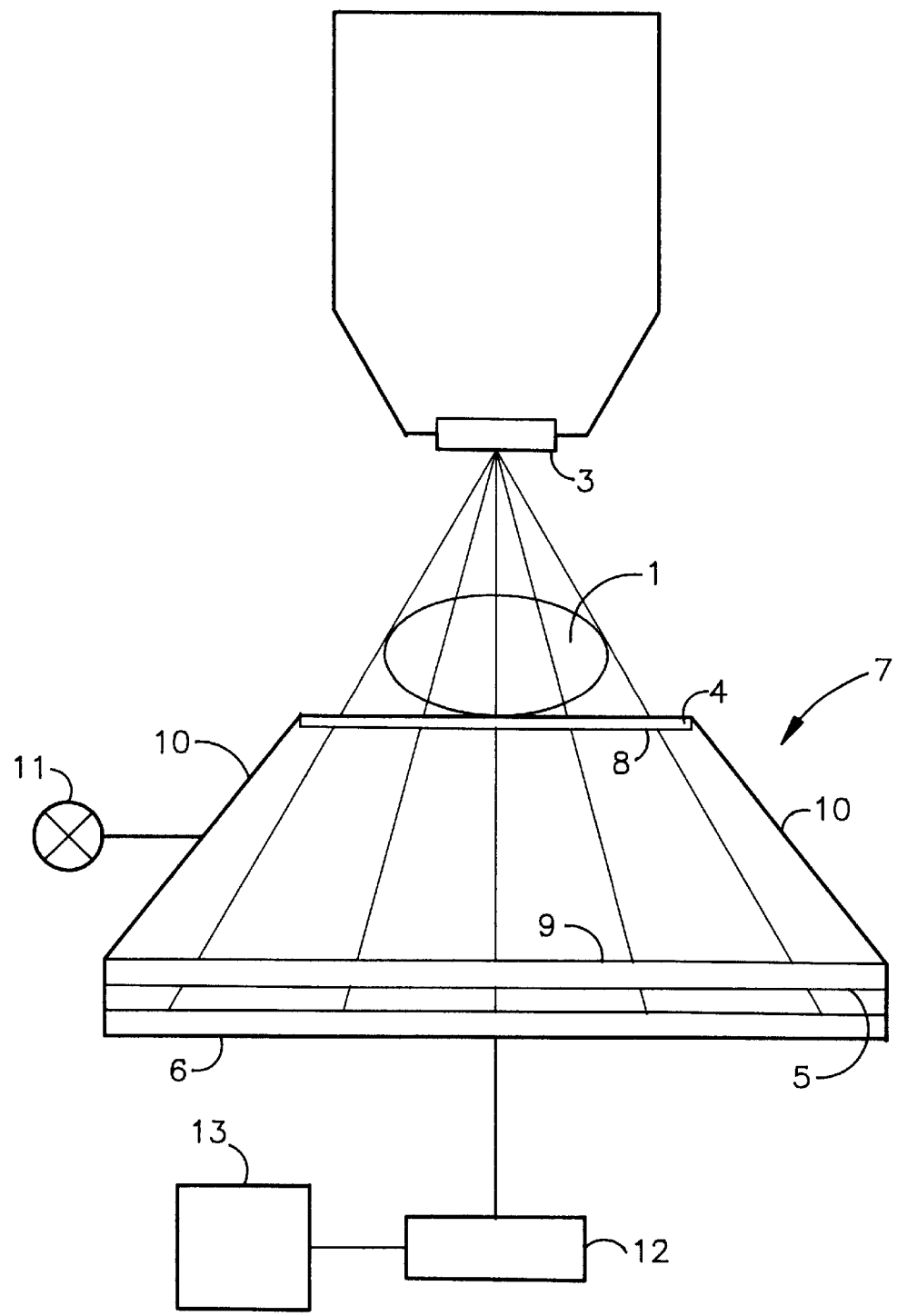
FIG. 5 is a drawing representing an embodiment of this invention wherein the detector and the space above the detector is enclosed and can be evacuated and/or filled or partially filled with a "low-z" gas.

FIG. 5 illustrates the multiwire detector 6, incorporated in an enclosed and sealed envelope 7, which is filled with a "low-z" gas. The detector 6 forms the base of the envelope. The top of the envelope can serve as the optional breast support 4, when used in mammography. The X-ray point source 3, and the object 1 are also shown for perspective.

The sealed envelope 7 has the top surface 8 and bottom surface 9 made from a material having small resistance to X-rays such as alumized nylon, aluminized Mylar (Trademark), aluminized Kapton (Trademark) and similar materials. The side wall 10 may be made of structural materials such as aluminum or of the same material as the top and bottom surfaces. A fill valve 11 for filling, removing and adjusting the gas, preferably helium, in the sealed envelope.

The detector 6 is connected to a computer 12 which uses an analog to digital converter to digitize the signals for use by the computer to provide a high resolution viewing screen 13.

The advantages of the present invention over the prior art include the primary advantage of overcoming the spatial resolution limits of many of the available electronic detection techniques, such as gas chambers or scintillating fiber-based detectors. Additional advantages which have been found are a higher rate capability by spreading the radiation over a larger detector surface and avoiding the space charge effect in gas chambers. This invention eases the requirement for 30–50 micron pixelation of the detector readout. Instead, the pixel sizes can be correspondingly increased proportionally with the magnification factor, this also includes demand for lower density electronics and/or lower count rates per channel.

The potential drawback of the increased object-detector distance related to the detection of scattered X-rays can be compensated, in the case of energy dispersive detectors, such as gas-based detectors, by rejection of scattered X-rays with an energy cut on the measured pulses.

When using the film technique which is not energy-dispersive there is no method to subtract the scattered events and this is the main reason why the geometry object-detector (film) must be kept as close as possible and the object (breast) is pressed against the film cassette. This requirement can be relaxed in the energy dispersive mode of operation possible with some electronic detectors, such as gas chambers. For example, using the practical magnification factor of 4.0 a resolution of 100–200 micron will be sufficient to obtain the required image resolution in applications such as mammography.

When the multiwire detector is integrated with a chamber defined by an envelope, the base of the envelope is preferably the same surface dimensions as the surface of the multiwire detector. The walls of the envelope are connected to the top surface plate which is parallel to the surface of the multiwire detector. This chamber is sealed from the atmosphere and can be evacuated and filled with a "low-z" gas as described above.

What is claimed is:

1. In a method for obtaining filmless radiological digital images of suitable resolution by exposing an object under study to a point source x-ray, allowing the x-rays to pass through the object under study to fall on the surface of a gas multiwire detector that is connected to a computer with a suitable imaging monitor, the object under study being at a distance from the gas multiwire detector such that the resolution of the image is enhanced through projection geometry, the improvement comprising placing a "low-z" gas in the area between the object under study and the gas multiwire detector.

2. The method of claim 1 wherein said "low-z" gas is helium.

3. The apparatus of claim 1 wherein a focusing grid is placed over and parallel to the surface of the multiwire detector.

4. The apparatus of claim 1 wherein said "low-z" gas is helium.

5. In an apparatus for use in filmless, digital, radiology comprising a point x-ray source located such that x-rays emanating from the x-ray source pass through an object under study and impinge the surface of a gas multiwire detector which is spaced from the object under study a sufficient distance to realize an enhanced resolution through projection geometry, the improvement comprising filling the space between the object under study and the gas multiwire detector with a "low-Z" gas.

* * * * *